(12) United States Patent
Ishibiki (10) Patent No.: US 6,565,505 B2
(45) Date of Patent: May 20, 2003

(54) ENDOSCOPE

(75) Inventor: Kouta Ishibiki, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/900,339

(22) Filed: Jul. 6, 2001

(65) Prior Publication Data

US 2002/0010385 A1 Jan. 24, 2002

(30) Foreign Application Priority Data

Jul. 11, 2000 (JP) ........................................ 2000-210193

(51) Int. Cl.[7] .................................................. A61B 1/00
(52) U.S. Cl. ........................ 600/133; 600/920; 600/139
(58) Field of Search ................................ 600/133, 920, 600/139, 140

(56) References Cited

U.S. PATENT DOCUMENTS

| | | | | |
|---|---|---|---|---|
| 5,443,057 A | * | 8/1995 | Elmore ........................ | 600/133 |
| 5,599,278 A | * | 2/1997 | Hibbard ....................... | 600/133 |
| 6,146,326 A | * | 11/2000 | Pollack et al. ............... | 600/133 |
| 6,328,691 B1 | * | 12/2001 | Rudischhauser ............ | 600/133 |

FOREIGN PATENT DOCUMENTS

| | | |
|---|---|---|
| JP | 8-56897 | 3/1996 |
| JP | 9-168503 | 6/1997 |

* cited by examiner

*Primary Examiner*—Linda C. M. Dvorak
*Assistant Examiner*—Jocelyn Ram
(74) *Attorney, Agent, or Firm*—Scully, Scott Murphy & Presser

(57) ABSTRACT

An endoscope comprises a plurality of members constituting the endoscope, and parts-bonded sections each having at least members thereof bonded together using an adhesive. The temperatures of thermal destruction at which the adhesives included in the parts-bonded sections are thermally destroyed are made equal to or higher than the maximum temperature attained during a high-pressure steam sterilization process. At the same time, the temperatures of thermal destruction are made equal to or lower than the heat-resistance temperatures above which members bonded using the adhesives or members located near the bonded members included in the parts-bonded sections fail to resist heat.

28 Claims, 3 Drawing Sheets

ENDOSCOPE

This application claims benefit of Japanese Application No. 2000-210193 filed in Japan on Jul. 11, 2000, the contents of which are incorporated by this reference.

BACKGROUND OF THE INVENTION

1. Field of the Invention

The present invention relates to an endoscope having parts-bonded sections each of which has members thereof bonded together using an adhesive.

2. Description of the Related Art

Endoscopes for medical use have been widely adopted in the past. The endoscope for medical use has an elongated insertion member thereof inserted into a body cavity in order to observe an intracavitary organ or has, if required, a therapeutic instrument passed through a therapeutic instrument channel thereof in order to perform any of various cures.

In particular, the endoscope for use in the medical field has an insertion member thereof inserted into a body cavity for the purpose of observation of an organ or has a therapeutic instrument passed through a therapeutic instrument channel thereof for the purpose of cures or treatments.

When a used endoscope or therapeutic instrument is reused for another patient, the endoscope equipment must be cleaned and sterilized after completion of examination or treatment in order to prevent inter-patient infection through the endoscope or therapeutic instrument.

In recent years, autoclaving (high-pressure steam sterilization) has become a mainstream of disinfection or sterilization of medical equipment. This is because autoclaving is no labor-intensive but is usable immediately after completion of sterilization and requires only a small running cost.

For example, Japanese Unexamined Patent Publication No. 8-56897 discloses a durable endoscope including a flexible sheathing tube that has portions thereof fastened using strings. The flexible sheathing tube will not be damaged despite contraction of the strings that derives from boiling sterilization or steam sterilization. The strings are short-fiber strings that are made of a synthetic resin and that exhibit a contraction ratio which is equal to or smaller than 14%. The contraction ratio is a ratio of the length of a string measured at the room temperature after the string is placed in steam of about 132° C. to the length thereof measured at the room temperature before the string is placed therein.

When the flexible sheathing tube is used to shield, for example, a bending section, an adhesive is applied to the short-fiber strings in order to secure the flexible sheathing tube. As the adhesive, an adhesive resistive to high temperature is used to enable high-pressure steam sterilization of the endoscope.

However, if the flexible sheathing tube should be broken, the flexible sheathing tube will be replaced with a new one. Otherwise, parts-bonded sections may be heated in order to destroy an applied adhesive so that the members included in the parts-bonded sections will be disassembled in order to replace a built-in component of an endoscope with a new one or repair it. In this case, the heating may deteriorate the flexible sheathing tube. Consequently, it may become very hard to dismount the flexible sheathing tube, or members located near the parts-bonded sections of the flexible sheathing tube may be broken with heat.

By the way, the parts-bonded sections may not be heated, but mechanical force may be applied to the parts-bonded sections in order to destroy the adhesive so that the members included in the parts-bonded sections can be disassembled. In this case, the members located near the parts-bonded sections may be broken with the mechanical force.

SUMMARY OF THE INVENTION

Accordingly, an object of the present invention is to provide an endoscope offering excellent workability. The endoscope can be sterilized with high-pressure steam and easily modified or repaired even after components are bonded using adhesives.

Briefly, according to the present invention, there is provided an endoscope consisting mainly of a plurality of members, which constitute the endoscope, and parts-bonded sections each of which has at least members thereof bonded together using an adhesive. The temperatures of thermal destruction at which the adhesives included in the parts-bonded sections are thermally destroyed are made equal to or higher than the maximum temperature attained during a high-pressure steam sterilization process. Besides, the temperatures of thermal destruction are made equal to or lower than the heat-resistance temperatures above which members bonded together using the adhesives or members located near the bonded members included in the parts-bonded sections fail to resist heat. When an endoscope is sterilized with high-pressure steam, the parts-bonded sections will not be degraded with high-pressure steam. Moreover, when a component of the endoscope must be repaired or modified, the adhesive included in the parts-bonded section must be destroyed with heat. At this time, the bonded members and the members located near the parts-bonded section will not be broken.

The above and other objects, features and advantages of the invention will become more apparent from the following description when taken in conjunction with the accompanying drawings.

DESCRIPTION OF THE PREFERRED EMBODIMENTS

An embodiment of the present invention will be described with reference to the drawings below.

Figure 1:
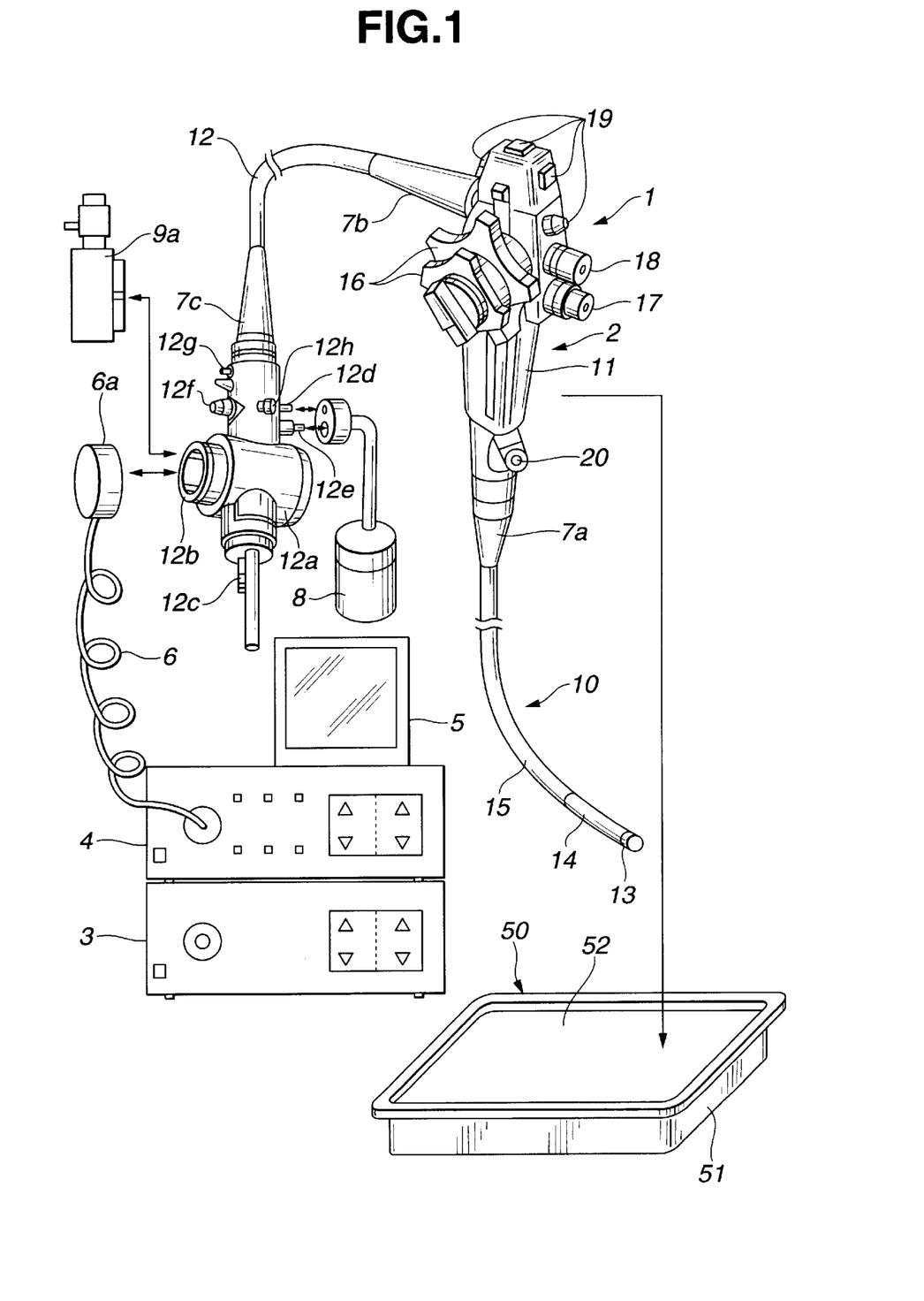
FIG. 1 is an explanatory diagram showing the outline configuration of a system including an endoscope in accordance with the present invention.

As shown in FIG. 1, an endoscope system 1 employed in an embodiment comprises an electronic endoscope (hereinafter simply an endoscope) 2, a light source apparatus 3, a video processor 4, and a monitor 5.

The endoscope 2 has an imaging means. The light source apparatus 3 supplies illumination light to the endoscope 2. The video processor 4 controls the imaging means, and processes an image signal generated by the imaging means, for example, a video signal. The video processor 4 is connected to the monitor 5. The endoscope 2 is stowed in a sterilization case 50 that will be described later.

The endoscope 2 comprises an insertion member 10, a control section 11, and a universal cord 12. The insertion member 10 is elongated and flexible. The control section 11 is coupled to the proximal end of the insertion member 10. The universal cord 12 is flexible and extended from the lateral part of the control section 11.

A connector 12a fixed to the end of the universal cord 12 is connected to the light source apparatus 3 so that it can be disconnected freely. When the connector 12a is connected to the light source apparatus 3, illumination light emanating from a lamp (not shown) included in the light source apparatus 3 is propagated over a light guide (not shown) run through the endoscope 2. The illumination light is then irradiated to a region to be observed.

An anti-insertion member breakage member 7a formed with an elastic member is included as a joint between the insertion member 10 and control section 11. The anti-insertion member breakage member 7a prevents abrupt bending. Moreover, an anti-control section breakage member 7b having the same structure as the anti-insertion member breakage member 7a is included as a joint between the control section 11 and universal cord 12. Furthermore, an anti-connector breakage member 7c having the same structure as the anti-insertion member breakage member 7a is included as a joint between the universal cord 12 and connector 12a.

The insertion member 10 of the endoscope 2 is made by concatenating a distal rigid part 13, a bending section 14, and a flexible tube 15 that is soft in that order from the distal end of the insertion member.

The distal rigid part 13 is formed with a rigid member. An observation window and an illumination window (not shown) are formed in, for example, the distal surface of the distal rigid part 13. Moreover, an opening of an aeration/perfusion nozzle through which cleaning fluid or gas is jetted to the observation window, and a suction port through which body fluid or filth is sucked are formed in the distal surface of the distal rigid part 13.

The bending section 14 has a plurality of bending pieces (not shown) concatenated and can be bent freely.

The flexible tube 15 is soft, elastic, and delicate.

The control section 11 has an angling knob 16. By properly manipulating the angling knob 16, the bending section 14 can be bent in a desired direction. In other words, the distal surface of the distal rigid part 13 in which the observation window or the like is formed can be angled in a desired direction by bending the bending section 14.

In addition to the angling knob 16, the control section 11 has an aeration/perfusion button 17 and a suction button 18, a plurality of remote-control switches 19, and a therapeutic instrument insertion port 20.

When the aeration/perfusion button 17 is pressed on a right occasion, cleaning fluid or gas is jetted out of the aeration/perfusion nozzle. Moreover, when the suction button 18 is pressed, body fluid or the like is sucked through the suction port. The plurality of remote-control switches 19 is used to remotely control, for example, the video processor 4. The therapeutic instrument insertion port 20 opens onto a therapeutic instrument channel tube, which will be described later, run through the insertion member of the endoscope 2.

An electric connector member 12b is formed on the lateral part of the connector 12a. A signal connector 6a fixed to a signal cord 6 that is coupled to the video processor 4 is mated with the electric connector member 12b so that it can be separated freely. When the signal connector 6a is mated with the electric connector member 12b, the video processor 4 controls the imaging means in the endoscope 2. Moreover, the video processor 4 processes an electric signal sent from the imaging means so as to generate a video signal. Consequently, an endoscopic view image is displayed on the screen of the monitor 5.

An air vent hole (not shown) that links the interior of the endoscope 2 and the exterior thereof is formed in the electric connector member 12b. A pressure regulating valve-inclusive waterproof cap (hereinafter simply a waterproof cap) 9a having a pressure regulating valve (not shown) that blocks the vent of the air vent hole can be freely detachably attached to the electric connector member 12b of the endoscope 2.

The connector 12a has an air supply base 12c, a water supply tank pressurization base 12d, a fluid supply base 12e, a suction base 12f, an injection base 12g, and a ground base 12h.

The air supply base 12c is connected to an air source (not shown) incorporated in the light source apparatus 3 so that it can be disconnected freely. The water supply tank pressurization base 12d and fluid supply base 12e are connected to a water supply tank 8, which is a fluid source, so that it can be disconnected freely. The suction base 12f is connected to a suction device (not shown) for sucking fluid through the suction port. The injection base 12g is connected to a water supplier (not shown) for supplying water. An electric cable is plugged in to the ground base 12h. Consequently, high-frequency leakage current developed during diathermy is fed back to a diathermy device (not shown).

The endoscope 2 can be cleaned after used for observation or treatment, and can be sterilized with high-pressure steam. Before the endoscope is sterilized with high-pressure steam, the waterproof cap 9a is attached to the electric connector member 12b. Moreover, before the endoscope 2 is sterilized with high-pressure steam, the endoscope 2 is stowed in the sterilization case 50.

The sterilization case 50 consists of a tray 51 that is a case body and a lid member 52. The tray 51 has a restriction member (not shown) contoured in conformity to the shape of the endoscope so that the components of the endoscope 2 including the insertion member 10, control section 11, universal cord 12, and connector 12a will be settled at predetermined positions. The tray 51 and lid member 52 each have a plurality of pours through which high-pressure steam is introduced into the case.

A porous compound membrane that does not infiltrate water but filtrates steam may be laid down in the tray 51, whereby cleaning fluid can be reserved in the tray 51. The compound membrane resists cleaning fluid. The tray 51 can therefore be used to clean the endoscope 2. After the endoscope 2 is cleaned, the endoscope 2 is settled in the tray 51 with the components thereof located at the predetermined positions. The sterilization casing 50 is placed in a high-pressure steam sterilizer, whereby the endoscope is sterilized.

Figure 2:
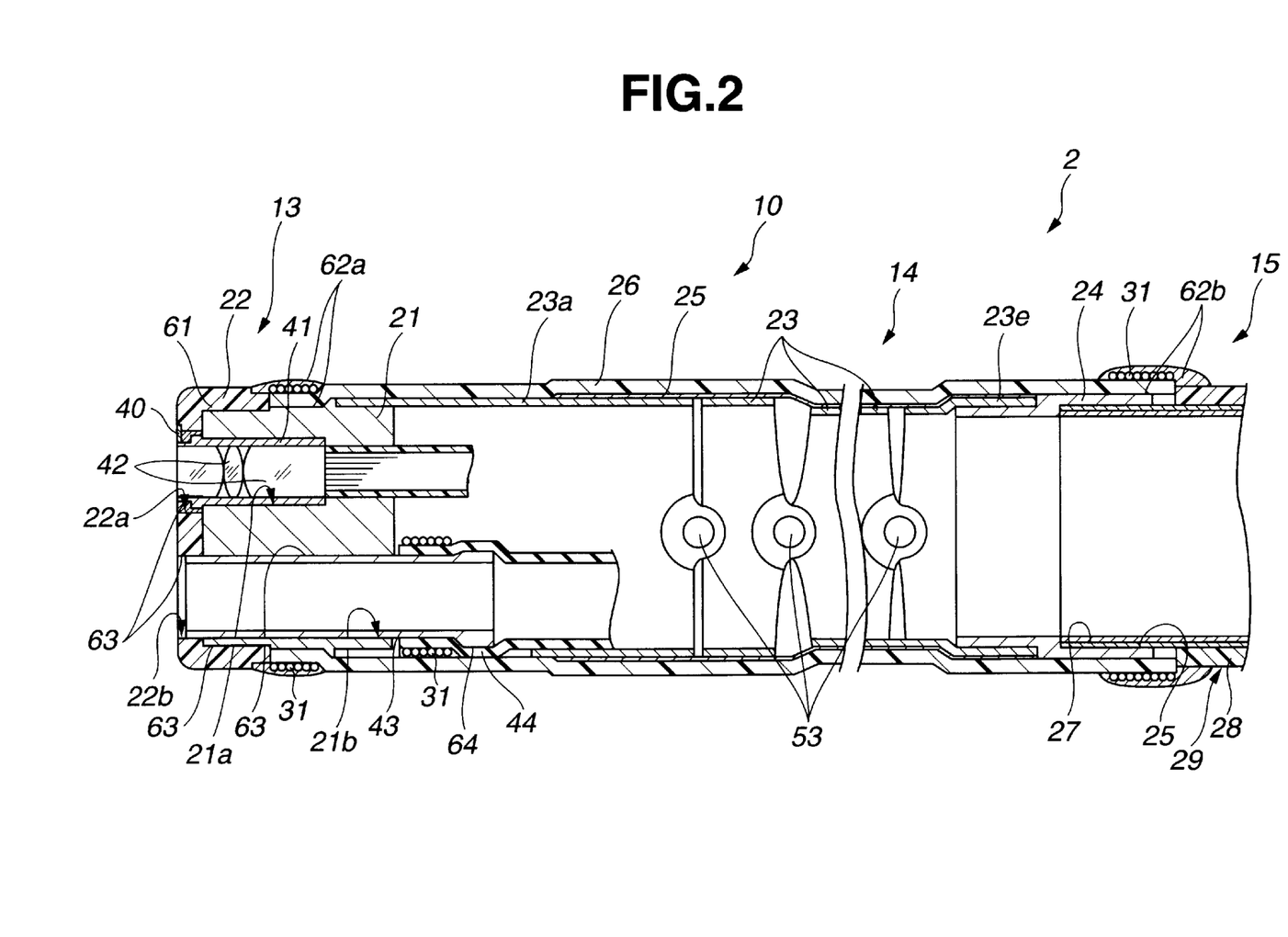
FIG. 2 is an explanatory diagram showing the structures of a distal rigid part and a bending section each including a parts-bonded section.

As shown in FIG. 2, the distal rigid part 13 of the insertion member 10 of the endoscope 2 has a distal body 21 formed with a metallic member made of, for example, SUS303 (stainless steel), that is, a rigid member. An isolation cover member 22 that is a housing member and a bonded member is bonded to the distal part of the distal body 21 using an adhesive 61.

The isolation cover member 22 is made of a resin that exhibits excellent chemical resistance against polyphenylsulfone, polysulfone, polyethersulfone, polyphenylene sulfide, polyether ether ketone, polyether imide, liquid crystal polymer, and polyamide imide, and resists high temperature equal to or higher than the temperature attained during a high-pressure steam sterilization process. In the present embodiment, the isolation cover member 22 is made of polyphenylsulfone.

Assuming that the temperature of thermal deformation serving as an index of heat resistance is defined as heat-resistance temperature above which a member fails to resist heat, a resin exhibiting the heat-resistance temperature of approximately 210° C. is adopted.

A distal bending piece 23a is fixed to the proximal end of the distal body 21 using a screw or the like. The distal bending piece 23a is the foremost one of the plurality of bending pieces 23 constituting the bending section 14.

A proximal bending piece 23e is the proximal one of the plurality of bending pieces 23 constituting the bending section 14. The proximal bending piece 23e is fixed to a distal base 24, which is made of, for example, SUS303, formed in the distal part of the flexible tube 15.

The bending pieces 23 are concatenated to one another using rivets 53 or the like so that they are rotatable freely. The concatenated bending pieces 23 are sheathed with a braid 25 made by plaiting metallic thin wires. The braid 25 is sheathed with a bending section sheathing tube (hereinafter simply a sheathing tube) 26 that is a bonded member.

The sheathing tube 26 is made of a resin such as a fluorocarbon rubber whose heat-resistance temperature is approximately 200° C. The distal part of the sheathing tube 26 covers the proximal part of the distal body 21, and the distal end face of the sheathing tube 26 is substantially abutted on the proximal end face of the isolation cover member 22. The proximal end of the sheathing tube 26 covers the distal base 24.

The flexible tube 15 is a bonded member and composed of a spiral tube 27, the braid 25, and a sheathing layer 28. The spiral tube 27 is made by spirally winding a metallic belt with a diameter held uniform. The spiral tube 27 is sheathed with the braid 25 made by plaiting metallic thin wires. The braid 25 is sheathed with the sheathing layer 28. The outer surface of the sheathing layer 28 is coated with a resin coating layer 29 made of, for example, a fluorocarbon resin.

The sheathing layer 28 is made of a resin, for example, a styrene resin, an ester-series thermoplastic elastomer, or an amide-series thermoplastic elastomer. According to the present embodiment, the ester-series thermoplastic elastomer resin is adopted as a base material, and a resin whose heat-resistance temperature is approximately 160° C. is mixed in the base material.

Moreover, the resin coating layer 29 is made using a fluorocarbon resin as a base material in which a resin whose heat-resistance temperature is approximately 200° C. is mixed. The distal end face of the sheathing layer 28 is substantially abutted on the proximal end face of the sheathing tube 26 that covers the distal base 24.

The edges of the outer surface of the sheathing tube 26 are fastened with a fixture string 31 that is wound about the edges of the outer surface. Consequently, the edges of the outer surface of the sheathing tube 26 are pressed and fixed to the distal body 21 and distal base 24 respectively that are located the inner surface side of the sheathing tube 26.

In the distal part side of the bending section, an adhesive 62a is applied to a gap between the inner surface of the sheathing tube 26 and the outer surface of the distal body 21. The sheathing tube 26 and distal body 21 are thus firmly bonded together. The adhesive 62a is also applied to the outer surface of the fastening string 31 so that it will fully shield the fixture string 31. This results in a parts-bonded section having the adhesive 62a applied to a section covering the edge of the isolation cover member 22 and the distal part of the sheathing tube 26.

Consequently, the fastening string 31 is shielded and protected, and the border between the isolation cover member 22 and sheathing tube 26 is sealed to be watertight.

On the other hand, in the proximal part side of the bending section, an adhesive 62b is applied to a gap between the inner surface of the sheathing tube 26 and the outer surface of the distal base 24. Thus, the sheathing tube 26 and distal base 24 are firmly bonded together. The adhesive 62b is also applied to the outer surface of the fastening string 31 so that it will fully shield the fastening string 31. This results in a parts-bonded section having the adhesive 62b applied to a section covering an edge of the resin coating layer 29, which coats the sheathing layer 28, and the proximal part of the sheathing tube 26.

Consequently, the fastening string 31 is shielded and protected, and the border between the flexible tube 15 and sheathing tube 26 is sealed to be watertight.

An illumination lens unit 40 is fitted in the distal body 21. The illumination lens unit 40 comprises a pipe-like illumination lens frame 41 made of a metal such as SUS303 and a group of illumination lenses 42 fixed in the illumination lens frame 41.

The illumination lens frame 41 is passed through a distal lens hole 21a and a cover member lens hole 22a. The distal lens hole 21a is formed in the distal body 21 along the axis of the distal body 21. The cover member lens hole 22a is formed in the isolation cover member 22. An adhesive 63 is applied to a gap between the illumination lens frame 41 and distal lens hole 21a and to a gap between the illumination lens frame 41 and cover member lens hole 22a. Thus, the illumination lens frame 41 is firmly boded to the distal lens hole 21a and to the cover member lens hole 22a.

A distal channel pipe hole 21b and a cover member channel pipe hole 22b are formed in the distal body 21 and isolation cover member 22 respectively. A metallic channel pipe 43 made of a metal such as SUS303 is passed through both the holes 21b and 22b. The adhesive 63 is applied to a gap between the channel pipe 43 and distal channel pipe hole 21b and to a gap between the channel pipe 43 and cover member channel pipe hole 22b. Thus, the channel pipe 43 is firmly bonded to the distal channel pipe hole 21b and to the cover member channel pipe hole 22b.

The distal part of a channel tube 44 that is a bonded member formed with an elongated tube made of polytetrafluoroethylene (PTFE) or the like is mounted on the outer surface of the proximal part of the channel pipe 43. The channel tube 44 is fastened with the fastening string 31. An adhesive 64 is applied to a gap between the channel tube 44 and channel pipe 43, whereby the channel tube 44 and channel pipe 43 are integrally bonded together. According to the present embodiment, the channel tube 44 is a tube whose heat-resistance temperature is approximately 260° C.

Figure 3:
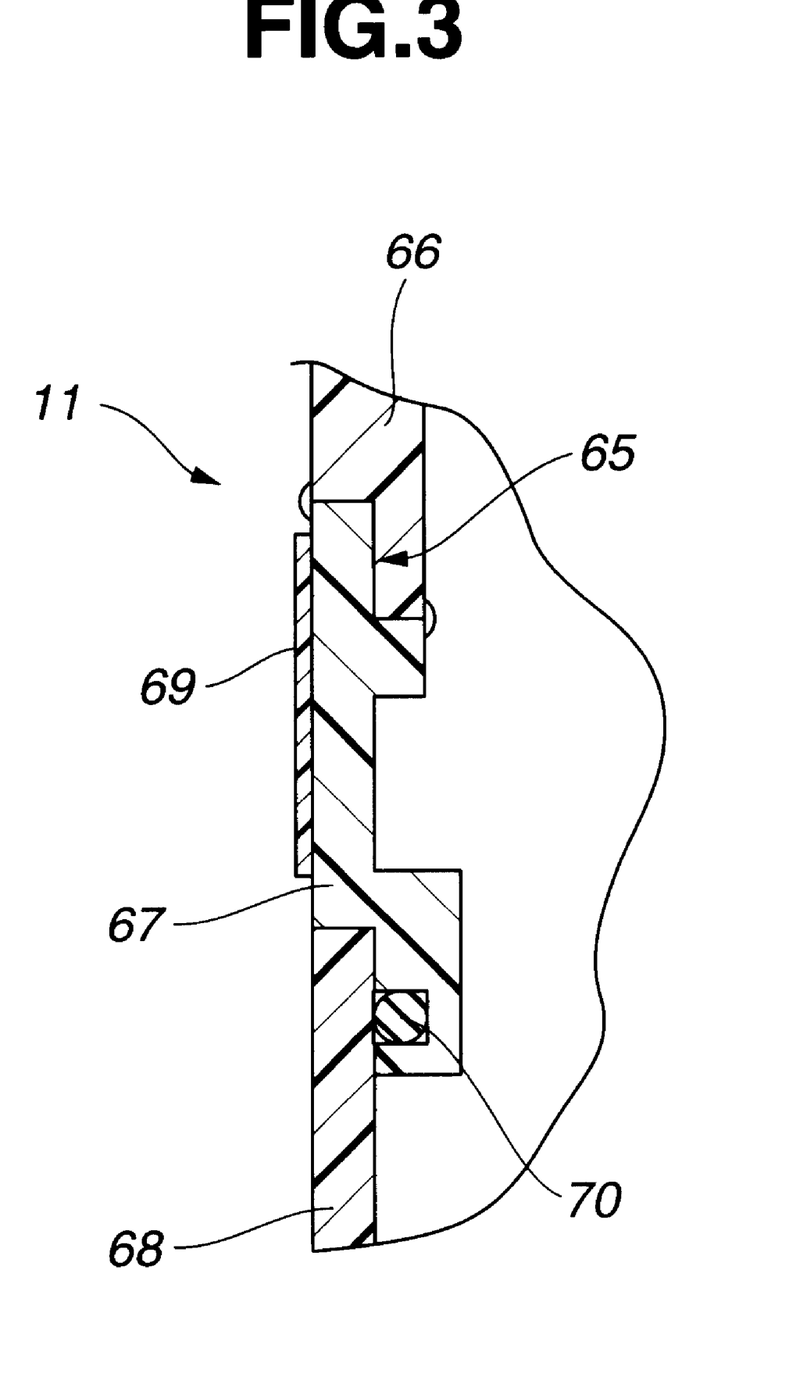
FIG. 3 is an explanatory diagram showing the structure of a parts-bonded section of a cover of a control section.

On the other hand, a bending mechanism (not shown) causing the bending section 14 to bend is incorporated in the control section 11. As shown in FIG. 3, the control section 11 is composed of a plurality of control section covers 66, 67, and 68 that are housing members.

The control section cover members 66, 67, and 68 are made of a resin that exhibits excellent chemical resistance against polyphenylsulfone, polysulfone, polyethersulfone, polyphenylene sulfide, polyether ether ketone, polyether imide, liquid crystal polymer, and polyamide imide. Besides, the resin resists high temperature equal to or higher than the temperature attained during a high-pressure steam sterilization process. In the present embodiment, the control section cover members 66, 67, and 68 are made of polyphenylene sulfide whose heat-resistance temperature is approximately 260° C.

The outer surface of the control section cover member 67 has a finished part 69 on which characters and symbols indicating a product name and others are inscribed through, for example, painting or printing. The finished part 69 is made of a material whose heat-resistance temperature is substantially identical to that of the resin material made into the control section cover member 67.

The control section cover member 66 and control section cover member 67 are integrally bonded together using an adhesive 65.

An O ring 70 is fixed to a position near a parts-bonded section that has the control section cover member 66 and control section cover member 67 bonded together using the adhesive 65, whereby the control section cover member 67 and control section cover member 68 are kept watertight. The O ring 70 is made of a fluorocarbon rubber and exhibits the heat-resistance temperature of approximately 250° C.

Now, the adhesives 61, 62, 63, 64, and 65 will be described below.

At first, the adhesives 62a and 62b will be described below. The adhesives 62a and 62b are applied to sections whose members are presumably disassembled highly frequently.

The adhesives 62a and 62b are, in the present embodiment, realized with the same adhesive 62 in consideration of workability in mounting the sheathing tube 26. The adhesive 62 has various additives mixed in an epoxy resin that is a base material. The property of the base material relative to a thermal load is thus changed. Consequently, when predetermined heat is applied to a parts-bonded section having two members bonded together using the adhesive 62, the bond strength of the adhesive is lowered to such an extent that the parts-bonded section can have members thereof disassembled. Incidentally, the predetermined heat to be applied in order to lower the bond strength, that is, the heating temperature at which the parts-bonded section is heated shall be referred to as the temperature of thermal destruction (hereinafter temperature H).

When the adhesive 62 is heated, the adhesive 62 can be easily destroyed, and the parts-bonded sections having members thereof bonded together using the adhesive 62 can have the members thereof readily disassembled. Assuming that the temperature of thermal destruction at which the adhesive 62 is thermally destroyed is H1, the temperature H1 is made equal to or larger than the maximum set temperature hmax at which the endoscope 2 is sterilized according to a high-pressure steam sterilization method. Moreover, the temperature H1 is made lower than the heat-resistance temperatures of bonded members that are bonded together using the adhesive 62, and the heat-resistance temperature of a member located near the bonded members included in the parts-bonded section. The bonded members include the sheathing tube 26, isolation cover member 22, distal body 21, sheathing layer 28 of the flexible tube 15, resin coating layer 29, and distal base 24. The member located near the bonded members included in the parts-bonded section is the channel tube 44.

Specifically, according to the present embodiment, the endoscope 2 is sterilized at 138° C. that is the maximum temperature attained during sterilization to be performed according to a typical high-pressure steam sterilization method. This means that the maximum set temperature hmax equals 138° C. Consequently, the temperature H1 of the adhesive 62 is made equal to or larger than 138° C.

Specifically, the temperature H1 of the adhesive 62 is made equal to or lower than the heat-resistance temperature of approximately 200° C. of the sheathing tube 26, the heat-resistance temperature of 210° C. of the isolation cover member 22, the heat-resistance temperature of 260° C. of the channel tube 44, the heat-resistance temperature of 160° C. of the sheathing layer 28 of the flexible tube 15, or the heat-resistance temperature of 200° C. of the resin coating layer 29. The heat-resistance temperature of the sheathing tube 26 is lower than that of SUS303 that is made into the distal body 21 and distal base 24. The temperature H1 is therefore made equal to or lower than 160° C. for fear the bonded members may be broken with heat. Consequently, the temperature H1 is determined to range from 138° C. to 160° C. (138° C.<H1<160° C.). In the present embodiment, therefore, the temperature H1 of the adhesive 62 is approximately 145° C.

The adhesives 61, 63, and 64 other than the adhesives 62a and 62b are applied to sections whose members are presumably disassembled less frequently than the sections to which the adhesives 62a and 62b are applied. Therefore, assuming that the temperature of thermal destruction at which the adhesives 61, 63, and 64 are thermally destroyed is H2, the temperature H2 is made higher than the temperature H1 of approximately 145° C. of the adhesives 61a and 62b, that is, the temperature H2 is approximately 160° C.

Assuming that the temperature of thermal destruction at which the adhesive 65 is thermally destroyed is H3, the temperature H3 is made equal to or higher than the maximum set temperature of 138° C. at which the endoscope 2 is sterilized during a high-pressure steam sterilization process. At the same time, the temperature H3 is made equal to or lower than the heat-resistance temperature of 260° C. of the control section cover members 66, 67, and 68 and of the finished part 69. Besides, the temperature H3 is made equal to or lower than the heat-resistance temperature of 250° C. of the O ring 70.

The temperature H3 is therefore made equal or lower than 250° C. for fear either of the bonded members may be destroyed with heat. Consequently, the temperature H3 is determined to range from 138° C. to 250° C. (138° C.<H<250° C.). In the present embodiment, therefore, the temperature H3 of the adhesive 65 is approximately 170° C.

Herein, typical conditions for high-pressure steam sterilization of the endoscope 2 will be described below.

As the conditions, the temperature and time for sterilization are stipulated in the standard ANSI/AAMI ST37-1992 recommended by the American National Standards Institute (ANSI) and published by the Association for the Advancement of Medical Instrumentation (AAMI). According to the standard, a pre-vacuum sterilization process should be performed at 132° C. for 4 min, and a gravity settling sterilization process should be performed at 132° C. for 10 min.

The condition of the temperature for high-pressure steam sterilization varies depending on the time for sterilization specified for a high-pressure steam sterilizer. In general, the temperature ranges from about 115° C. to 138° C. However, some sterilizers can be set to about 142° C.

On the other hand, the time for sterilization varies depending on the condition of the temperature for sterilization. In general, the time ranges from about 3 min to about 60 min. Some types of sterilizers can be set to about 100 min.

The pressure in a sterilization chamber to be attained during sterilization is generally set to +0.2 Mpa approximately against the atmospheric pressure.

Next, a typical pre-vacuum high-pressure steam sterilization process for endoscopes will be described briefly.

The typical pre-vacuum high-pressure steam sterilization process includes a pre-vacuum step and a sterilization step. At the pre-vacuum step, a sterilization chamber in which equipment to be sterilized is placed is decompressed prior to the sterilization step. At the sterilization step, high-pressure high-temperature steam is fed into the sterilization chamber in order to sterilize an endoscope.

The pre-vacuum step is a step of making preparations for causing steam to reliably permeate the details of the equipment to be sterilized at the sterilization step. At the pre-vacuum step, the sterilization chamber is decompressed so that high-pressure high-temperature steam will permeate the equipment to be sterilized. At the pre-vacuum step, the pressure in the sterilization chamber is lower than the atmospheric pressure by a value ranging from about −0.07 MPa to about −0.09 MPa.

Some types of sterilizers are designed to dry (perform a dry step) the equipment to be sterilized with the sterilization chamber decompressed again after completion of sterilization. In this case, at the dry step, the sterilization chamber is decompressed in order to exhaust steam from the sterilization chamber. This facilitates drying of the equipment to be sterilized. At the dry step, the pressure in the sterilization chamber is lower than the atmospheric pressure by a value ranging from about −0.07 Mpa to about −0.09 MPa. Incidentally, the dry step is arbitrarily performed if required.

As described above, the interior and exterior of the insertion member 10 of the endoscope 2 are exposed to high-pressure steam at the sterilization step. However, the temperatures H of the adhesive 62 and adhesives 61, 63, 64, and 65 are 145° C., 160° C., and 170° C. respectively. The parts-bonded sections formed by applying the adhesives 61, 62, 63, 64, and 65 respectively will therefore not deteriorate due to high-pressure steam.

The sheathing tube 26 of the bending section 14 serves as a housing member of the endoscope 2. Compared with the other members, the sheathing tube 26 is likely to be broken due to piercing or the like. If the sheathing tube 26 were, for example, pierced, it should be replaced with a new one. The replacement will be described below.

If the sheathing tube 26 is pierced, the parts-bonded sections formed at both ends of the sheathing tube 26 using the adhesives 62a and 62b are broken by destroying the adhesives. At this time, the parts-bonded sections are heated using a heating means, for example, a heat gun.

The heating temperature at which the parts-bonded sections are heated at this time is approximately 155° C. In other words, the heating temperature is slightly higher than the temperature H1 of the adhesives 62a and 62b that is approximately 145° C. At the same time, the heating temperature is lower than the heat-resistance temperatures of the sheathing tube 26, distal body 21, isolation cover member 22, distal base 24, sheathing layer 28, resin coating layer 29, and channel tube 44.

When the parts-bonded sections formed using the adhesives 62a and 62b are heated at 155° C., the parts-bonded sections are broken with the adhesives destroyed. When the parts-bonded sections formed using the adhesives 62a and 62b are heated, the temperature of heat passed to the sheathing tube 26, distal body 21, isolation cover member 22, distal base 24, sheathing layer 28, and resin coating layer 29 is lower than the heat-resistance temperatures of these members. Therefore, during the heating, these members will be neither fused nor carbonized, or anyhow, will not be broken. The parts-bonded sections alone are broken, and the sheathing tube 26 can be dismounted easily.

Moreover, the isolation cover member 22 and flexible tube 15 that are neither fused nor carbonized, or anyhow, is unaffected by heating can be reused.

When the adhesive 62a applied to the distal end of the sheathing tube 26 is heated, the channel tube 44 located near the heated section is also heated at substantially the same temperature. However, the temperature is lower than the heat-resistance temperature of the channel tube 44. The channel tube 44 is therefore not broken during the heating but can be reused.

Moreover, the temperature at which the parts-bonded sections formed using the adhesives 62a and 62b are heated is lower than the heat-resistance temperatures of the adhesives 61, 63, and 64 applied near the parts-bonded sections. The parts-bonded sections formed using the adhesives 61, 63, and 64 will therefore not be broken with the adhesives destroyed during the heating.

In other words, when the adhesives 62a and 62b are destroyed with heat, the parts-bonded sections formed using the adhesives 61, 63, and 64 need not have members thereof bonded together again.

Furthermore, when the bending section 14 or the illumination lens unit 40 fitted in the distal body 21 or an imaging optical unit (not shown) must be repaired or replaced with a new one, the sheathing tube 26 must be dismounted first.

The sheathing tube 26 and the housing members located around the sheathing tube 26 will not be broken with heat. Therefore, after an intended member is repaired or replaced with a new one, the sheathing tube 26 and surrounding housing members can be reused.

Moreover, if the sheathing tube 26 should be pierced in the process of manufacturing the endoscope 2, or if the sheathing tube 26 slackens, a new sheathing tube 26 must be mounted or the sheathing tube 26 must be re-mounted. Even in this case, similarly to when the intended member must be repaired or replaced with a new one, the sheathing tube 26 can be replaced or repaired easily.

When the isolation cover member 22 must be replaced with a new one because it is broken, the parts-bonded sections are heated at the temperature that is slightly higher than the heat-resistance temperature of the adhesive 61 which is approximately 160° C., and that is lower than the heat-resistance temperature of the isolation cover member 22 of 210° C. The temperature is, for example, 165° C.

At this time, the temperature of heat passed to the isolation cover member 22 is lower than the heat-resistance temperature of the isolation cover member 22. The isolation cover member 22 will therefore be neither fused nor carbonized, or anyhow, will not be broken with heat. The isolation cover member 22 can be readily dismounted from the distal body 21. Moreover, the surrounding members will remain unaffected.

Moreover, the channel tube 44 located near the heated sections is heated at substantially the same temperature. However, the heating temperature is lower than the heat-resistance temperature of the channel tube 44. The channel tube 44 will therefore not be broken but can be reused.

Furthermore, the temperatures H of the adhesives may be made higher than the heat-resistance temperature of 210° C. of the isolation cover member 22. However, in this case, even if the isolation cover member 22 is broken with heat, the smoothness in dismounting the isolation cover member 22 must not be degraded and the other members must be held unaffected. Specifically, the temperatures H are made lower than the heat-resistance temperature of 260° C. of the channel tube 44, or in other words, determined to range from 210° C. to 260° C. (210° C.<H<260° C.). Consequently, the temperatures H are made equal to, for example, 220° C.

Consequently, when the adhesive 61 is destroyed with heat, the isolation cover member 22 that is a member to be replaced with a new one may be broken. However, the channel tube 44 will not be broken but can be reused.

When a plurality of parts-bonded sections is located mutually closely, the temperature H of an adhesive used to form one parts-bonded section whose members are presumably repaired or disassembled highly frequently is made lower than the temperature H of an adhesive used to form the other parts-bonded sections whose members are presumably disassembled less frequently. Thus, even when one parts-bonded section has members thereof disassembled, the other parts-bonded sections will not be broken.

Consequently, when a section whose members are presumably disassembled highly frequently has the members thereof disassembled, parts-bonded sections whose members are presumably disassembled less frequently are reliably prevented from being destroyed.

By the way, when a bending mechanism (not shown) incorporated in the control section must be repaired, the parts-bonded section having the control section cover member 66 and control section cover member 67 bonded together using the adhesive 65 is heated at 180° C. to destroy the adhesive.

The parts-bonded section is thus broken, whereby the control section cover member 66 and control section cover member 67 are separated from each other in order to repair the bending mechanism. At this time, the temperature of heat passed to the control section cover members 66, 67, and 68, the finished part 69 of the control section cover member 67, and the O ring 70 is lower than the heat-resistance temperatures of the members. Therefore, the members will be neither fused nor carbonized, or anyhow, will not be broken. Otherwise, painting or printing performed on any member will not deteriorate. After the bending mechanism is repaired, it can be assembled again and reused.

According to the present embodiment, a parts-bonded section can be heated at predetermined temperature so that the members of the parts-bonded section can be disassembled easily. The bonded members included in a parts-bonded section and a member located near the parts-bonded section are prevented from being mechanically loaded or broken with a load. Any work can be carried out reliably.

The temperature of thermal destruction at which an adhesive to be applied to bond members is thermally destroyed is equal to or higher than the maximum set temperature at which the endoscope is sterilized during a high-pressure sterilization process. At the same time, the temperature of thermal destruction falls within a range of values smaller than the heat-resistance temperatures of bonded members that are bonded together using the adhesive and the heat-resistance temperatures of a member located near a parts-bonded section composed of the bonded members. Consequently, the parts-bonded section can be reliably prevented from deteriorating because it is exposed to high-pressure steam during the high-pressure steam sterilization process.

Moreover, if a bonded member malfunctions, the bonded member must be replaced with a new one or repaired. In this case, once the parts-bonded section including the bonded member is heated at predetermined temperature, the bonded member that malfunctions can be modified or repaired. At this time, the malfunctioning bonded member or a member located nearby will not be broken with heat.

Moreover, when a bonded member is repaired, a member having a finished layer whose heat-resistance temperature is relatively low or a member made of a resin will not be broken. Members other than the malfunctioning bonded member can be reused. The repairing expense can be held low.

Furthermore, the temperature of thermal destruction of an adhesive applied to a section whose members are presumably disassembled highly frequency is lower than the temperature of thermal destruction of an adhesive applied to a section whose members are presumably disassembled less frequently. Therefore, when a component whose members are presumably repaired or disassembled highly frequently, for example, the sheathing of the bending section or the like has members thereof disassembled, the other components will not be broken but the component can be modified or repaired easily and inexpensively.

Moreover, when a section has members thereof disassembled, the members can be disassembled easily. Besides, an expensive component having a finished layer, that is, having part thereof painted, printed, metallically finished, or optically coated will not be broken, but a malfunctioning member can be modified or repaired easily.

Furthermore, the material of bonded members or the material of a member located near a parts-bonded section composed of the bonded members can be selected from among a wide range of materials. Moreover, a method of finishing can be selected from among a wide range of methods.

According to the present embodiment, when a malfunctioning component must be repaired or replaced with a new one, the malfunctioning component, a component bonded to the malfunctioning component, or a component located near the parts-bonded section composed of these components will not be broken with heat. The components other than the malfunctioning component can be reused.

Moreover, housing members that are presumably disassembled highly frequently in order to repair an incorporated-in component or replace it with a new will not be broken with heat generated for disassembling. The malfunctioning component can therefore be modified or repaired easily and inexpensively. This results in an endoscope capable of being easily manufactured or repaired.

Incidentally, when the heat-resistance temperature of an adhesive is set, consideration must be taken into the heat-resistance temperature of a material itself. In addition, the heat-resistance temperatures of an agent used to finish the surface of an aluminum member or the like, of an agent used to finish the surface of a metallic member, of a agent used to paint or print a metallic or resin member, and of an agent used to optically coat the surface of an optical member such as the group of illumination lens 42 must be taken into consideration. The agent used to finish the surface of an aluminum member or the like is, for example, anodized aluminum oxalate, anodized aluminum sulfate, or chromate.

Moreover, if the temperatures of thermal destruction of adhesives are substantially the same as the temperature attained during a high-pressure steam sterilization process, the heat-resistance temperatures of bonded members and those of members located near parts-bonded sections including the bonded members are lower.

Consequently, the freedom in selecting a material to be made into a member is expanded, and an inexpensive material or a mechanically superb material can be selected. For example, when the endoscope 2 is designed to resist the temperature typically attained during a high-pressure steam sterilization process, since the temperature attained during the high-pressure steam sterilization process is 138° C., the temperatures of thermal destruction of adhesives are set to range from 140° C. to 150° C. (140° C.~150° C.).

Furthermore, when ceramic-series adhesives are adopted, the adhesives exhibit excellent heat resistance. However, the heat-resistance temperatures of the adhesives are very high. Therefore, the adhesives may not be able to exhibit the properties that are a constituent feature of the present invention. Similarly to the aforesaid embodiment, when an epoxy resin is adopted as a base, adhesives can be produced to exert the properties that are a constituent feature of the present invention. Moreover, the adhesives offer great bond strength and excellent chemical resistance, and are inexpensive. This leads to improved workability in assembling.

The present invention is not limited to the aforesaid embodiment. The present invention may be adapted to any parts-bonded section in an endoscope, a casing member, or a tube that is presumably repaired highly frequently. The casing member shields an internal mechanism of a connector unit that serves as a joint between the endoscope and external apparatuses. The tube may be a water supply channel, a fluid supply channel, or a channel tube through which fluid is fed and which are run through the endoscope. The present invention will prove quite effective when adapted to, especially, the following sections: a section that is exposed on the surface of the endoscope and likely to be broken with external force or a chemical; a section whose members are disassembled in order to repair an incorporated-in component of the endoscope; or a section including housing members that are presumably disassembled highly frequently.

Moreover, generally, the higher the heat-resistance temperatures of adhesives, the shorter the time required for high-pressure steam sterilization. When the heat-resistance temperatures of adhesives are made equal to or higher than 132° C., the sterilization time is shortened. When the heat-resistance temperatures are made equal to 140° C., a sterilizer that sterilizes an endoscope at the highest possible temperature at present can be adopted. Consequently, the sterilization time can be shortened.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. An endoscope comprising:

two or more parts having parts bonded sections; and two or more adhesives for connecting any combination of the two or more parts at their corresponding parts bonded sections:

wherein a temperature of thermal destruction H1 at which one of the two or more adhesives is thermally destroyed is lower than a temperature of thermal destruction H2 at which another of the two or more adhesives is thermally destroyed, and wherein H1 and H2 are equal to or higher than a maximum temperature attained during a high-pressure steam sterilization process, and equal to or lower than heat-resistance temperatures above which two of the two or more parts bonded together using one of the two or more adhesives fail to resist heat.

2. An endoscope according to claim 1, wherein when at least one of said two or more parts located near said parts-bonded sections are reused after being disassembled for the purpose of repair, a temperature of thermal destruction of a corresponding adhesive is equal to or lower than heat-resistance temperatures of the two or more parts that are reused.

3. An endoscope according to claim 2, wherein said two or more parts located near said parts-bonded sections are selected from a group consisting of parts having a finished layer and parts made of a resin.

4. An endoscope according to claim 3, wherein said finished layer is selected from a group consisting of a painted coating, a printed coating, a metallic coating and an optical coating.

5. An endoscope according to claim 1, wherein at least one of the two or more parts are housing members that constitute an outer surface of said endoscope.

6. An endoscope according to claim 5, wherein said housing member is a bendable sheathing tube of a bending section for sheathing the bending section included in an insertion member of said endoscope.

7. An endoscope according to claim 5, wherein said housing member is a flexible tube that is an integral part of an insertion member of said endoscope.

8. A An endoscope according to claim 1, wherein said parts-bonded sections are sections whose corresponding parts are disassembled frequently.

9. An endoscope according to claim 1, wherein at least one of said two or more adhesives have an epoxy resin base.

10. An endoscope according to claim 1, wherein at least one of said two or more parts is a casing member for one of shielding an internal mechanism incorporated in a control section of said endoscope or in a connector unit thereof serving as a joint between said endoscope and at least one external apparatus.

11. An endoscope according to claim 1, wherein at least one of said two or more parts is a resin isolation cover member included in a distal side of an insertion member of said endoscope.

12. An endoscope according to claim 1, wherein at least one of said two or more parts is a channel tube through which fluid is fed and which runs through said endoscope.

13. An endoscope comprising:

a first part composed of material which exhibits heat resistance up to a first predetermined temperature;

a second part composed of material which exhibits heat resistance up to a second predetermined temperature which is equal to or higher than said first predetermined temperature;

a first parts-bonded section in which said first part and said second part are bonded together using a first adhesive;

a third part composed of material which exhibits heat resistance up to a third predetermined temperature which is equal to or higher than said first predetermined temperature;

a fourth part composed of material which exhibits heat resistance up to a fourth predetermined temperature which is equal to or higher than said third predetermined temperature; and a second parts-bonded section in which said third part and said fourth part are bonded together using a second adhesive;

wherein the first adhesive used in bonding of said first parts-bonded section exhibits heat resistance at a heat-resistance temperature equal to or higher than the maximum temperature attained during a high-pressure steam sterilization process and equal to or lower than first predetermined temperature; and the second adhesive used in bonding of said second parts-bonded section exhibits heat resistance at a heat-resistance temperature equal to or higher than the maximum temperature attained during a high-pressure steam sterilization process and equal to or lower than the third predetermined temperature of said third part, and exhibits the heat resistance at the temperature different from that at which said first adhesive used in bonding of said first parts-bonded section exhibits the heat resistance.

14. An endoscope according to claim 13, wherein the heat-resistance temperature of the second adhesive used in bonding of said second parts-bonded section is equal to or higher than the heat-resistance temperature of the first adhesive used in bonding of said first parts-bonded section.

15. An endoscope according to claim 14, wherein the first and second parts of said first parts-bonded section are disassembled at least as many times as the third and fourth parts of said second parts-bonded section.

16. An endoscope according to claim 13, wherein at least one of the first, second, third, and fourth parts are made of a resin.

17. An endoscope according to claim 16, wherein at least one of the first and second adhesives have an epoxy resin base.

18. An endoscope according to claim 16, wherein at least one of said first, second, third, and fourth parts are reused after being disassembled for the purpose of repair, a temperature of thermal destruction of the corresponding first and/or second adhesive is equal to or lower than a heat-resistance temperature of the parts that are reused.

19. An endoscope according to claim 16, wherein at least one of the first, second, third, and fourth parts are housing members that constitute an outer surface of said endoscope.

20. An endoscope according to claim 16, wherein at least one of said first and second parts-bonded sections are sections whose corresponding parts are disassembled frequently.

21. An endoscope according to claim 16, wherein at least one of said first, second, third, and fourth parts is a casing member for shielding an internal mechanism incorporated in a control section of said endoscope or in a connector unit thereof serving as a joint between said endoscope and at least one external apparatus.

22. An endoscope according to claim 13, wherein at least one of the first, second, third, and fourth parts have a finished layer on which metal welding cannot be effected.

23. An endoscope according to claim 22, wherein said finished layer is provided by any of painting, printing, metallic finishing, and optical coating.

24. An endoscope according to claim 22, wherein at least one of the first and second adhesives have an epoxy resin base.

25. An endoscope according to claim 22, wherein at least one of said first, second, third, and fourth parts are reused after being disassembled for the purpose of repair, a temperature of thermal destruction of the corresponding first and/or second adhesive is equal to or lower than heat-resistance temperatures of the parts that are reused.

26. An endoscope according to claim 22, wherein at least one of the first, second, third, and fourth parts are housing members that constitute an outer surface of said endoscope.

27. An endoscope according to claim 22, wherein at least one of said first and second parts-bonded sections are sections whose corresponding parts are disassembled frequently.

28. An endoscope according to claim 22, wherein at least one of said first, second, third, and fourth parts is a casing member for shielding an internal mechanism incorporated in a control section of said endoscope or in a connector unit thereof serving as a joint between said endoscope and at least one external apparatus.

* * * * *